(12) United States Patent
Hopkins et al.

(10) Patent No.: US 7,230,697 B2
(45) Date of Patent: Jun. 12, 2007

(54) METHOD AND APPARATUS FOR MULTI-MODE SPECTRAL IMAGING

(75) Inventors: Mark F. Hopkins, Tucson, AZ (US); Yashvinder Sabharwal, Tucson, AZ (US); Cynthia Vernold, Tucson, AZ (US)

(73) Assignee: Roper Industries, Inc., Sarasota, FL (US)

( * ) Notice: Subject to any disclaimer, the term of this patent is extended or adjusted under 35 U.S.C. 154(b) by 80 days.

(21) Appl. No.: 11/040,709

(22) Filed: Jan. 20, 2005

(65) Prior Publication Data

US 2005/0157294 A1 Jul. 21, 2005

Related U.S. Application Data

(60) Provisional application No. 60/537,839, filed on Jan. 21, 2004.

(51) Int. Cl.
*G01J 3/28* (2006.01)
(52) U.S. Cl. .................. 356/328; 356/317; 356/419
(58) Field of Classification Search ........ 326/320–334; 356/317, 318, 419, 417
See application file for complete search history.

(56) References Cited

U.S. PATENT DOCUMENTS

| | | | |
|---|---|---|---|
| 5,127,728 A | 7/1992 | Warren et al. | |
| 5,539,517 A | 7/1996 | Cabib et al. | |
| 5,926,283 A | 7/1999 | Hopkins | |
| 5,982,497 A | 11/1999 | Hopkins | |
| 6,128,077 A * | 10/2000 | Jovin et al. | 356/310 |
| 6,166,373 A | 12/2000 | Mao | |
| 6,816,258 B2 * | 11/2004 | Hutchin | 356/328 |
| 7,042,567 B2 * | 5/2006 | Balas et al. | 356/326 |
| 2005/0030533 A1 * | 2/2005 | Treado | 356/326 |

OTHER PUBLICATIONS

"Spectral imaging and its applications in live cell microscopy", Timo Zimmerman, Jens Rietdorf, and Rainer Pepperkok, FEBS Letters 543, Advanced Light Microscopy Facility and Cell Biology/Cell Biophysics Programme, Heidelberg, Germany (May 2003) pp. 87-92.

* cited by examiner

*Primary Examiner*—Layla G. Lauchman
(74) *Attorney, Agent, or Firm*—Caesar, Rivise, Bernstein, Cohen & Pokotilow, Ltd.

(57) ABSTRACT

A method and apparatus is disclosed for multi-mode spectral imaging. In one embodiment, the present invention comprises the steps of illuminating an object with a modified illumination profile, producing a reflected, transmitted or fluorescence image of the illuminated object, scanning the object, and re-imaging the reflected, transmitted or fluorescence light after modifying the light's optical state. The present invention preferably works in conjunction with other imaging systems to provide both high-spectral resolution images with lower temporal resolution and multiple image acquisition with high temporal resolution.

18 Claims, 11 Drawing Sheets

Optical State 1  Optical State 2

Optical State 1  Optical State 2

Optical State 3  Optical State 4

METHOD AND APPARATUS FOR MULTI-MODE SPECTRAL IMAGING

REFERENCE TO RELATED DOCUMENTS

This invention claims priority to, and the benefit of, U.S. Provisional Patent Application Ser. No. 60/537,839, entitled "Slit-Scanning Confocal Imaging Spectrometer", filed Jan. 21, 2004, the entire contents of which are hereby incorporated by reference.

TECHNICAL FIELD OF INVENTION

This invention applies broadly to the area of spectroscopic systems and imaging spectrometry. More specifically, the present invention comprises a multi-mode spectral imaging method and apparatus allowing for the spectroscopic evaluation of an object while maintaining the spatial integrity of the image being evaluated. This method, in one embodiment, provides for the acquisition of a series of spectrally-discrete, two-dimensional images in conjunction with at least one other optical system such as a microscope or a fundus camera. The resulting data cube provides high-resolution spectral and spatial information at each pixel in the image. The confocal nature of the device provides high-resolution spatial imagery, improving contrast by rejecting light from image planes within the object volume that are not in focus.

BACKGROUND OF THE INVENTION

In general, spectroscopic systems allow for the determination of the spectral (i.e., wavelength) composition of an object or a scene. Generally, these systems collect the total light coming from or emitted by the object. The wavelengths that comprise the collected light are typically separated with the use of a dispersive element employing refractive means such as a prism or diffractive means (such as, for example, a grating). After being reflected by or transmitting through one of these dispersive elements, the different wavelength components of the light propagate in different directions, and their intensities are recorded by a one-dimensional array of detector pixels. While standard spectrometers are excellent devices for determining the spectral composition of all the light emanating from an object, they are typically unable to provide two dimensional spatial maps of the spectra emanating from an object.

The present invention generally falls within the category of imaging spectrometers. Imaging spectrometers are more sophisticated than standard spectrometers because they allow for the measurement of the wavelength composition of light coming from each point in the object. Imaging spectrometers providing high spectral resolution (i.e. less than 2 nm) are known in the art as either "spectral scanning" or "spatial scanning" systems.

Spectral scanning systems typically take a series of images, where each image represents a full field-of-view, two-dimensional representation of the object, comprised of light within a certain spectral bandpass. Separate wavelength images are taken one after the other, or sequentially in time. Specific systems for spectral scanning include those incorporating liquid crystal tunable filters (LCTF), acoustic optical tunable filters (AOTF), and interferometric systems such as the Fourier transform spectrometer (FTS) and the Fabry-Perot spectrometer (FPS).

With LCTF-based systems, the properties of the liquid crystals are adjusted to "tune" the spectral bandpass of the filter. In this way, different, full field-of-view, spectral images are obtained over time. These systems have a number of disadvantages. For example, these systems are polarization-sensitive and, as a result, they have low transmission efficiency, resulting in significant light loss. As another example, the minimum spectral bandpass is usually 10 nm or greater. This is the result of the physics of the LCTF and a practical limitation imposed by the significant light loss. Therefore, high-spectral resolution (less than 2 nm) imaging is rarely possible with these systems. When AOTFs are used as tunable bandpass filters, AOTF-based systems have similar disadvantages.

An FTS system is usually based on the design of a Twyman-Green interferometer or a Sagnac interferometer (such as disclosed in U.S. Pat. No. 5,539,517), both of which are typically used to ascertain the spectral content of a point source. In typical operation for this type of system, a positive lens collimates the light from the point source before it enters the interferometer. Either a test arm or reference arm mirror is scanned along the optical axis with the intensity being detected at each scan position. Taking the inverse Fourier transform of the envelope of the detected signal yields the spectral intensity of the object as a function of frequency or wavelength.

An FPS system is based on another interferometric design that generally employs two highly reflective mirrors to form an optical cavity that functions as a spectral filter. In this type of a system, collimated light entering this system will undergo multiple reflections within the optical cavity. As a result of this configuration, only the particular wavelength component for which all the multiple reflections interfere constructively will pass through the optical cavity to be recorded by a detector. The particular wavelength that is passed by the optical filter depends on the distance between the two highly reflective mirrors. As this distance is changed, the wavelength passed by the filter also changes. Thus, the spectral bandpass of the FPS system is a function of the lateral separation of the mirrors. In this way, as one mirror is scanned along the optical axis, effectively changing the distance between the mirrors, the spectral bandpass is changed and the different spectral components of the source are recorded sequentially by the detector.

The FTS and FPS systems are also capable of performing imaging spectrometry and determining the spectral composition of an object on a point-by-point basis. However, there are certain limitations imposed by the physical geometry of these systems. In addition, in both cases, the system field of view is restricted. For example, with regard to the FTS system, the length of the system, combined with the small size of the mirrors, restricts the field of view because optical rays will not propagate through the system for large angles. Therefore, the number of points on an object which can be acquired is limited. Another problem arises with respect to image registration. Two-dimensional images are acquired as one of the mirrors is scanned. Problems associated with scanning, such as mirror jitter, uneven scanning, or beam-walking, create registration problems between the images in the different spectral bands. With regard to the FPS system, it is also limited to a small field of view because of two main effects. For example, the light coming from the source undergoes multiple reflections within the mirrored optical cavity before emerging from the system. When the incident light comes from an off-axis point on the object, it enters the cavity at an incident angle other than zero. Consequently, as the light undergoes multiple reflections, it will walk along the mirrors and eventually leak out of the cavity. The result of this behavior is that as the field increases, the light throughput of the system decreases. Another problem with the FPS configuration has to do with spectral bandpass variation with field. Since the effective mirror separation changes with field angle, so does the spectral bandpass. To minimize this field-dependent spectral variation, the field of view must necessarily be small.

Typically spectral scanning systems suffer from the fact that their inherent design does not allow for confocal imaging of the object. Confocal imaging systems always require some sort of spatial scanning. Spectral scanning systems have no spatial scanning attribute, making confocal microscopy impossible.

In addition, all spectral scanning systems have a fundamental flaw when used in low light applications such as fluorescence microscopy. These applications suffer from a phenomenon called photobleaching, where the fluorescence of an object decreases with the length of the exposure, and phototoxicity, where the light that is used to illuminate the object is toxic to the object. In all spectral scanning systems the entire object must be illuminated the entire time the wavelength scan is taking place. As a result, the images acquired later in the sequence (i.e. the longer wavelength images) will be dimmer than the images acquired first because of photobleaching. This change in intensity is not something that can easily be corrected after acquisition of the images. If toxicity becomes an issue, then the object's characteristics will change over time as the object becomes damaged. This effect cannot be corrected for post acquisition.

Spatial scanning systems, achieve the same result as the spectral scanning systems, but without the drawbacks discussed. Spatial scanning systems are optical imaging systems where a portion of a two-dimensional object is imaged onto a detector. Spatial scanning systems are usually classified into two types, based on the dispersion mechanism used. There are prism-based systems (such as disclosed in U.S. Pat. No. 5,127,728) and grating-based systems. In typical spatial scanning systems, a dispersive element in the optical path spreads the wavelength components of each point in the image along one dimension of a detector. This behavior effectively creates a series of rainbows on the detector. When a prism is used, the dispersion is achieved via refraction of the light. Alternatively, when a grating is used, the dispersion is achieved via diffraction of the light. Prism-based systems have the advantage of higher light throughput than grating-based systems. However, prism-based systems have the significant disadvantage of producing non-linear dispersion, requiring data correction via interpolation for proper visualization and processing. Since the dispersion effect via refraction is not as pronounced as it is via diffraction, prism-based systems generally require longer optical trains to achieve the same unit dispersion as grating-based systems. Grating-based systems display linear dispersion, eliminating the data correction step. The dispersion is higher than prism-based systems, which makes the optical trains shorter, but the efficiencies slightly lower than prism-based systems.

Gratings can be reflective or transmissive. Reflective gratings that utilize metal coatings for their reflectivity are used often for imaging spectrometers in a design configuration known as the Czerny-Turner configuration. This configuration utilizes a symmetric optical design with two spherical mirrors and a planar reflective grating. The symmetry of the design minimizes optical aberration's; however, to obtain a reasonable field-of-view, the optical train tends to be long, preventing the development of a compact system. Furthermore, the reflective gratings used in the Czerny-Turner configurations are usually made with metal coatings that are quite polarization sensitive, meaning P-polarized light will yield a different result than S-polarized light. This causes a significant problem in fluorescence microscopy applications that are often, by their nature, highly polarization-dependent processes. Transmission gratings and reflective gratings that utilize "polarization insensitive" coatings do not present the same problems because they are not significantly polarization sensitive. As disclosed in the present invention, more compact designs can be utilized to obtain sizable fields of view.

In order to achieve spatial scanning, stages (such as motorized stages, for example) are used to move the object from one position to the next to create a two dimensional image. In some instances, the object is held fixed while the illumination is scanned and the detection aperture is scanned in conjunction with the detector (such as disclosed in U.S. Pat. No. 6,166,373). These approaches are generally very slow and do not have the necessary accuracy or temporal resolution for live-cell microscopy imaging applications.

Finally, all of these high-spectral resolution imaging systems are only capable of providing high-spectral resolution with low temporal resolution. In many instances, it is desirable to use high-spectral resolution to identify an optimal smaller set of wavelengths which are then acquired instantaneously on a single or multiple detectors (i.e. high temporal resolution). One example of the usefulness of a single, multi-mode spectral imaging system in microscopy is discussed in "Spectral imaging and its applications in live cell microscopy", Timo Zimmerman, Jens Rietdorf, and Rainer Pepperkok, FEBS Letters 543, Advanced Light Microscopy Facility and Cell Biology/Cell Biophysics Programme, Heidelberg, Germany (May 2003) pages 87–92.

While different methods may be used to achieve imaging spectrometry, the prior art is generally not capable of providing the required performance within a compact, modular, flexible and fast system. The prior art also fails to disclose providing multiple imaging modalities within a single system.

There is a significant need for a compact, modular, flexible and fast system, which is adapted to provide different imaging modalities within a single system for microscopy. The present invention satisfies this need.

SUMMARY OF THE INVENTION

The following summary of the invention is provided to facilitate an understanding of some of the innovative features unique to the present invention, and is not intended to be a full description of variations that may be apparent to those of skill in the art. A full appreciation of the various aspects of the invention can be gained from the entire specification, claims, drawings, and abstract taken as a whole.

The present invention is a spectral imaging method and apparatus for acquiring multi-dimensional images. In one embodiment, the present invention comprises a method for multi-mode spectral imaging of an object comprising the steps of illuminating the object with a modified illumination profile, producing a reflected, transmitted or fluorescence image of the illuminated object, scanning the object, and re-imaging the reflected, transmitted or fluorescence light after modifying the light's optical state.

One embodiment employs a grating to disperse the light and a piezoelectric crystal-based stage for spatial scanning of the object. The grating subassembly is preferably removable, allowing full-field imaging, or replaceable by an optical beamsplitting module, thereby allowing simultaneous acquisition of multiple component images having different optical properties. At least one aperture illuminates a portion of the object being evaluated (the same portion that is being imaged), allowing for confocal operation and minimization of photobleaching artifacts and phototoxicity.

The novel features of the present invention will become apparent to those of skill in the art upon examination of the following detailed description of the preferred embodiment or can be learned by practice of the present invention. It should be understood, however, that the detailed description of the preferred embodiment and the specific examples presented, while indicating certain embodiments of the present invention, are provided for illustration purposes only because various changes and modifications within the spirit and scope of the invention will become apparent to those of skill in the art from the detailed description, drawings and claims that follow.

BRIEF DESCRIPTION OF THE DRAWINGS

The accompanying figures further illustrate the present invention and, together with the detailed description of the preferred embodiment, assist to explain the general principles according to the present invention.

Additional aspects of the present invention will become evident upon reviewing the non limiting embodiments described in the specification and the claims taken in conjunction with the accompanying figures, wherein like reference numerals denote like elements.

DETAILED DESCRIPTION OF THE PREFERRED EMBODIMENT

Figure 1:
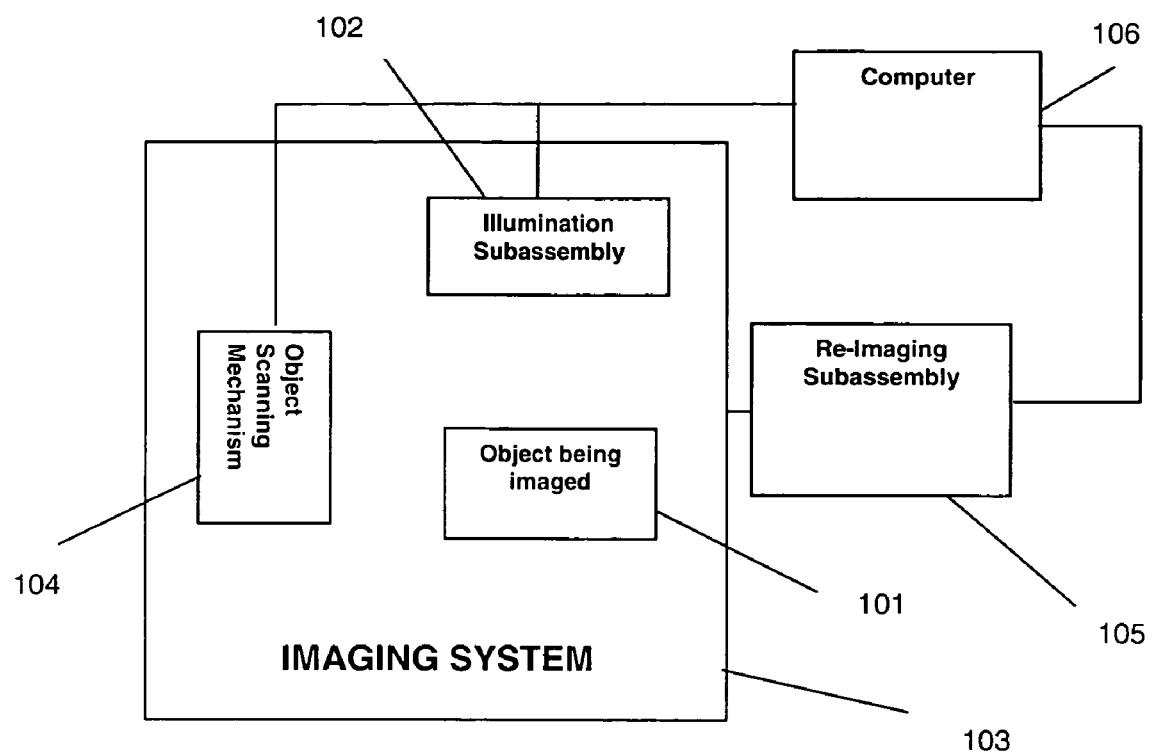
FIG. 1 illustrates an exemplary block diagram of the multi-mode spectral imaging method and apparatus.

The present invention is a multi-mode spectral imaging method and apparatus for acquiring multi-dimensional images. The present invention allows for the creation of at least one image data cube corresponding to the same two-dimensional image at more than one wavelength, polarization or intensity. This data cube, in one embodiment, may be produced in two modes. In mode #1, multiple high-spatial resolution images are acquired simultaneously at either a small number of wavelengths (low spectral resolution), a small number of polarization states, or a small number of intensities, thereby achieving high temporal resolution images. In mode #2, the object is scanned in time to produce high-spatial resolution images, with high spectral resolution. However, due to the scanning nature of mode #2, the temporal resolution is limited by the scan rate. When critical illumination conditions are satisfied, mode #2 can be operated with the additional feature of confocal imaging. All imaging modes address the need to separate the light emanating from the object into components of different optical states. The different operating modes of the present invention allow the flexibility to select different components as the experiment may require, and to record images of the highest quality while minimizing light induced damage to the object. The ability to provide all of these imaging modes within a single apparatus is of tremendous significance as it alleviates errors which are always introduced when different apparatus have to be used for different measurements.

In the figures used to illustrate the various aspects of the present invention, the coordinates x and y are used to describe the plane orthogonal to the optical axis of the spectrometer. The x and y axes correspond to the horizontal and vertical directions, respectively. The z coordinate corresponds to the direction along the optical axis of the device.

For the purposes of this disclosure, the optical state of a wavefront is defined as the combination of the wavefront's amplitude, phase, polarization, and frequency (wavelength). An optical filter is defined as any component such as a spectral or neutral density filter or a polarizer that modifies the optical state of an incident wavefront. A beamsplitter is defined as any optical component that separates a single optical beam into more than one optical beam. Examples include, but are not limited to, dichroic filters (wavelength separation), polarization beamsplitters (polarization separation), and amplitude beamsplitters (amplitude/intensity separation). A dispersive element is defined as any component that resolves incident light into its component wavelengths. For purposes of this disclosure, a grating is defined as any polarization insensitive dispersive element which uses diffraction as the method of dispersing the light. Examples of gratings include, but are not limited to, planar gratings, blazed gratings, volume holographic gratings, or acousto-optic tunable filters (AOTF). The term critical illumination is defined to represent an optical illumination configuration where illumination light is focused on the object.

In one embodiment as seen in FIG. 1, the present invention's method comprises the following four steps, not necessarily in any particular order: illuminating the object 101 with a modified illumination profile, producing a reflected, transmitted or fluorescence image of the illuminated object 101, scanning the object 101, and re-imaging the reflected, transmitted or fluorescence light after modifying the light's optical state. The image produced by the step of re-imaging may be visualized using a computer 106 or some other viewing device.

A representative apparatus 103 for achieving the step of producing a reflected, transmitted or fluorescence image of the object being evaluated may include, various optical systems, such as objective lenses, microscopes or fundus cameras. The apparatus should preferably be adapted to illuminate the object and form a reflected, transmitted, or fluorescence image of the illuminated object. While the step of producing the image is known in the art, the specific steps disclosed in this invention of allowing multiple modes of spectral imaging within a single apparatus have never heretofore been disclosed.

The step of illuminating the object with a modified illumination profile provides light to the object which is then reflected, transmitted, or absorbed and re-emitted as fluorescence. Furthermore, this step modifies the illumination profile produced at the object location. In a fluorescence microscope system, for example, this has the significant advantage of limiting photobleaching and phototoxicity of the object because only those areas being imaged are illuminated. Furthermore, when modification of the illumination profile limits the spatial extent of the illumination, a confocal effect results by removing light from out of focus image planes, improving image contrast and resolution. When modification takes the form of focusing the illumination beam on the object to produce critical illumination, there is a corresponding increase in the energy density of illumination and further enhancement of the confocal effect. As those of skill in the art know, the use of critical illumination also reduces the output power requirements for the illumination source.

Figure 2A:
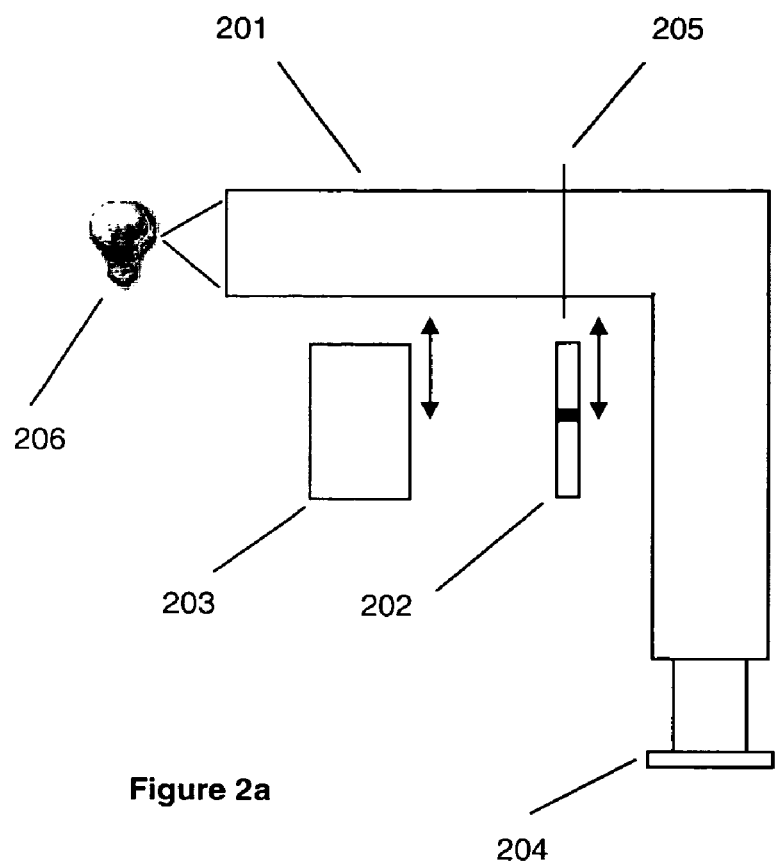
FIG. 2a illustrates a diagram of an exemplary illumination arm of an optical system identified in FIG. 1 such as a microscope (unmodified)
Figure 2B:
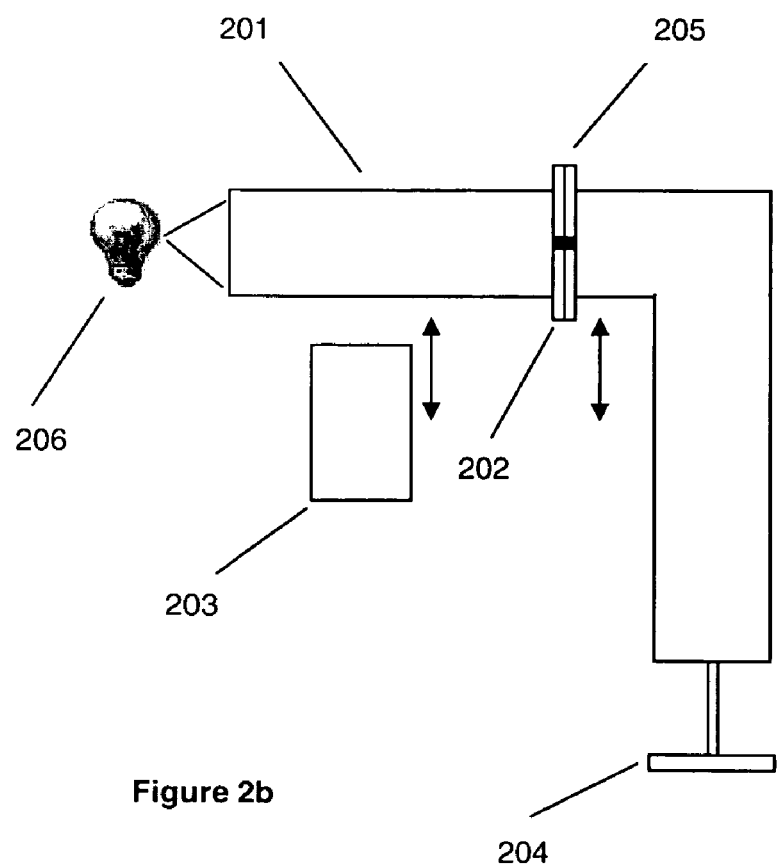
FIG. 2b illustrates a diagram of another exemplary illumination arm of an optical system identified in FIG. 1 such as a microscope with a single-slit adjustable aperture placed at a field stop location.
Figure 2C:
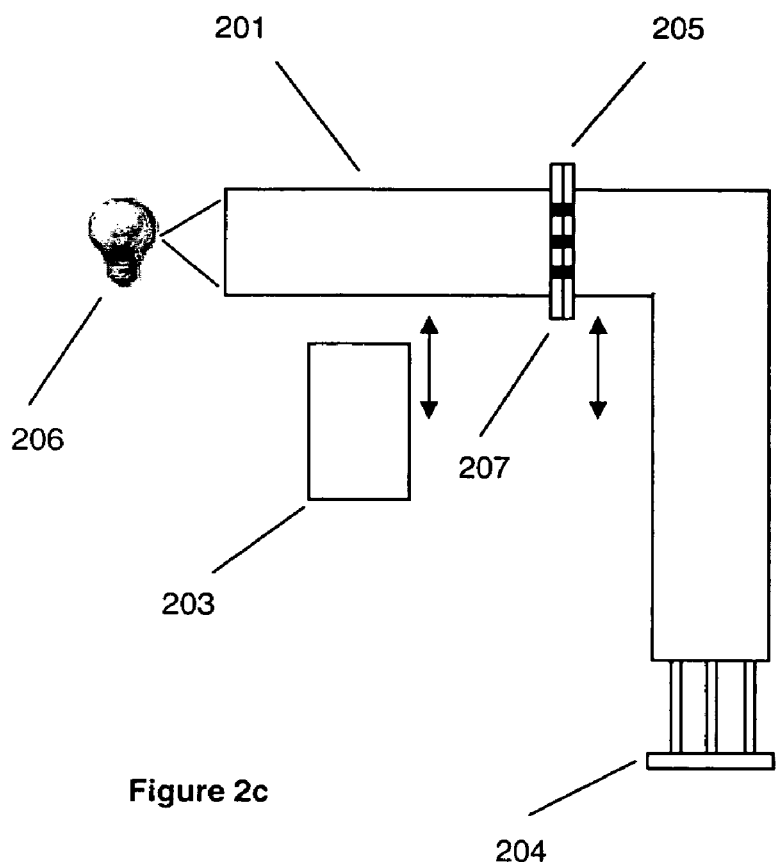
FIG. 2c illustrates a diagram of another exemplary illumination arm of an optical system identified in FIG. 1 such as a microscope with a multiple-slit adjustable aperture placed at a field stop location.

A representative apparatus 201 for achieving the step of illuminating the object with a modified illumination profile may include at least one adjustable aperture 202,207 and at least one optical assembly 203. In one embodiment, the adjustable aperture 202,207 may be placed at a field stop 205 of the illumination optical system 201 of the microscope or other optical instrument. An aperture 202,207 (such as a single-slit aperture 202) placed in the field stop 205, for example, will limit the spatial extent of the illumination profile on the object 204. In one example of this embodiment, the use of an adjustable slit aperture 202 (as illustrated in FIG. 2b) allows for a thin, rectangular-shaped area on the object 204 to be illuminated. Alternatively (as illustrated in FIG. 2c), an aperture with multiple slits 207 may be employed, which achieves the benefit of data multiplexing, because data may be acquired from multiple spatial regions on the object 204 simultaneously, effectively reducing total object scan times.

Figure 2D:
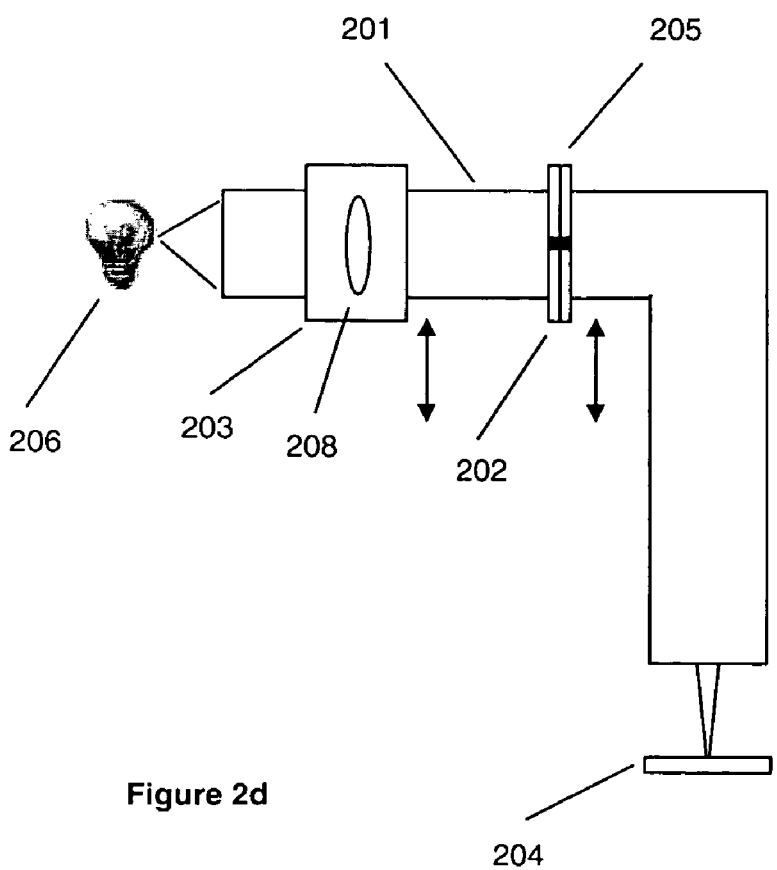
FIG. 2d illustrates a diagram of another exemplary illumination arm of an optical system identified in FIG. 1 such as a microscope with a single-slit adjustable aperture placed at a field stop location and an optical assembly placed in the illumination path to achieve critical illumination.
Figure 2E:
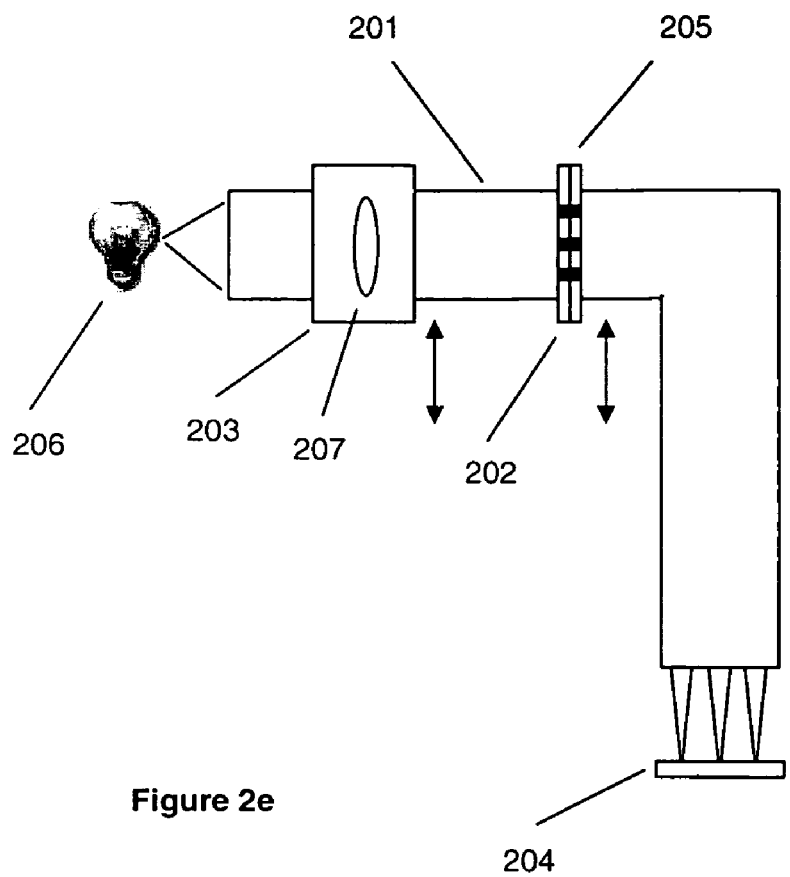
FIG. 2e illustrates a diagram of another exemplary illumination arm of an optical system identified in FIG. 1 such as a microscope with a multiple-slit adjustable aperture placed at a field stop location and an optical assembly placed in the illumination path to achieve critical illumination.
Figure 2F:
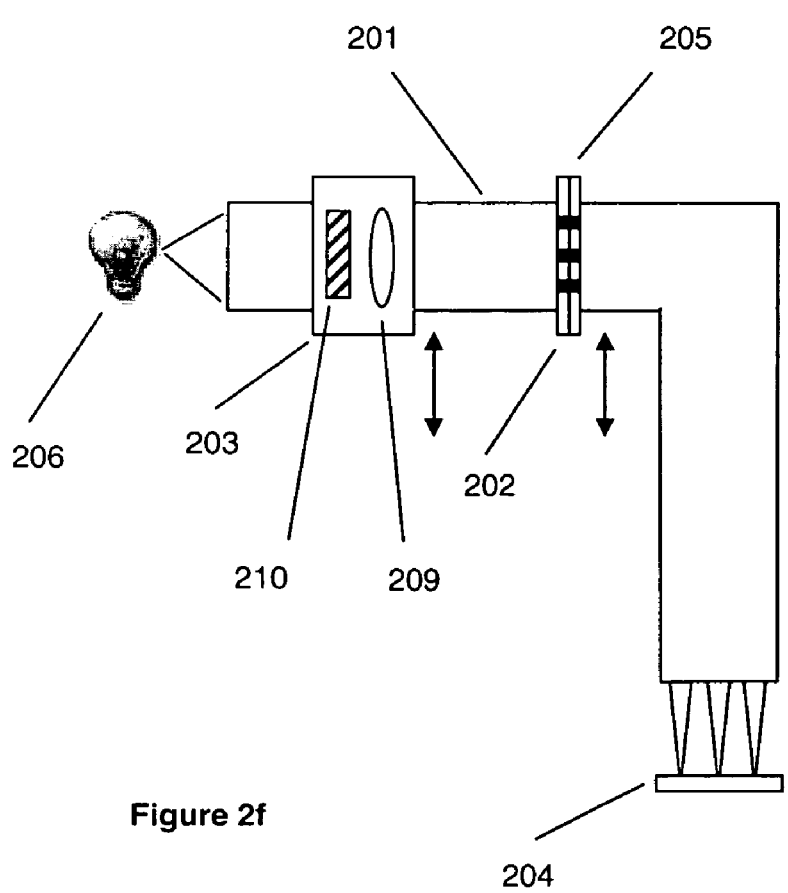
FIG. 2f illustrates a diagram of another exemplary illumination arm of an optical system identified in FIG. 1 such as a microscope with a multiple-slit adjustable aperture placed at a field stop location and an optical assembly incorporating a diffractive optical component placed in the illumination path to achieve critical illumination.

A representative optical assembly 203 may be situated between the light source 206 of the microscope or an image of the light source, or other optical system, and the field stop 205 of the illumination system 201. The representative optical assembly 203 should be adapted for receiving the light coming from the source assembly 206, which is preferably pseudo-collimated, and focusing the illumination profile to match the pattern of the adjustable aperture 202,207. For an adjustable aperture 202,207, a representative optical assembly 203 may utilize a combination of refractive 209 and diffractive 210 optical components to yield a spatial pattern matching the pattern of the adjustable aperture 202,207 at the field stop 205 (as shown, for example, in FIGS. 2d–2f).

Figure 3A:
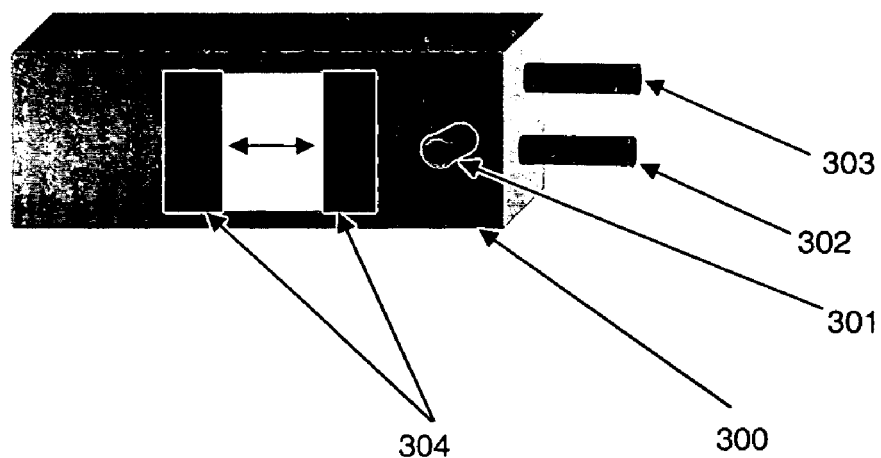
FIG. 3a illustrates an exemplary manual version of the adjustable aperture of the illumination subassembly.
Figure 3B:
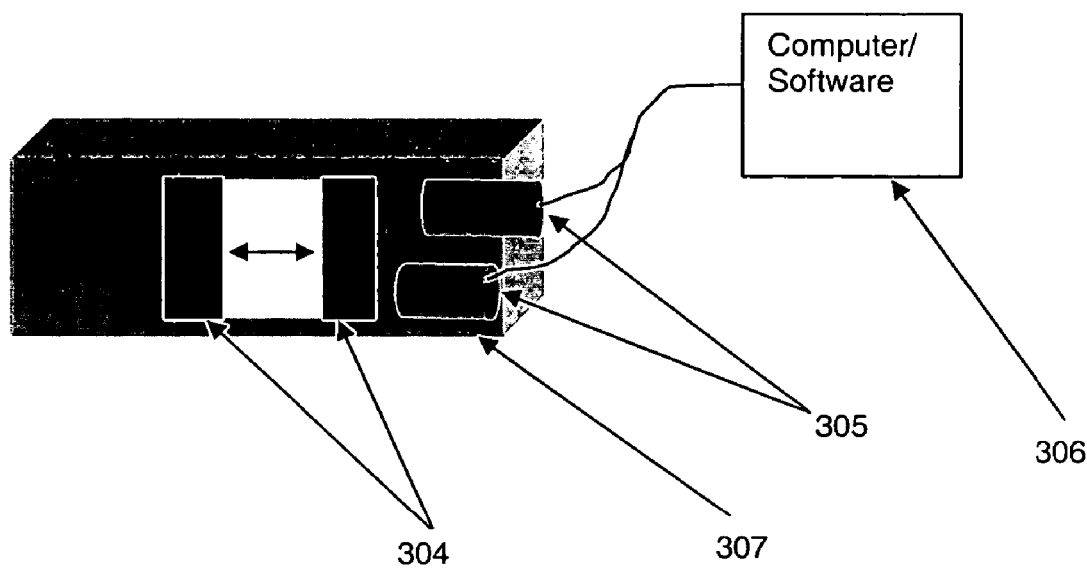
FIG. 3b illustrates an exemplary motorized version of the adjustable aperture of the illumination subassembly.

A representative adjustable aperture of the illumination subassembly is, in one embodiment, adapted to be controlled manually or electronically, (such as with, for example, an electronically-controlled motor). As seen in FIG. 3a, in the manual control embodiment 300, adjustment knobs 301,302, 303 may be provided for accurate positioning of the aperture 304. The aperture 304 is preferably adjustable at micrometer level accuracies. Alternatively, in the motorized control embodiment 307 (as illustrated in FIG. 3b), stepper motors 305 may be controlled by software or hardware (or a combination thereof 306) to precisely adjust the position and size of the aperture(s) 304. Both the aperture apparatus 202,207 and the optical subassembly 203 are preferably removable. When the aperture 202,207 and optical 203 subassemblies are in the optical path, such that the illumination profile is modified, then confocal operation is achieved; however, when standard illumination is desired, these subassemblies may be removed to produce an unmodified illumination profile to the object.

Mode #2 operation of the present invention is preferably adapted to acquire an image of each point in the object with high spectral resolution. In order to create a data cube, scanning of the object is required. In the preferred embodiment of this method, the object is moved in very small increments (e.g., micrometer or sub-micrometer increments) to acquire the spatial information of the object.

Figure 4:
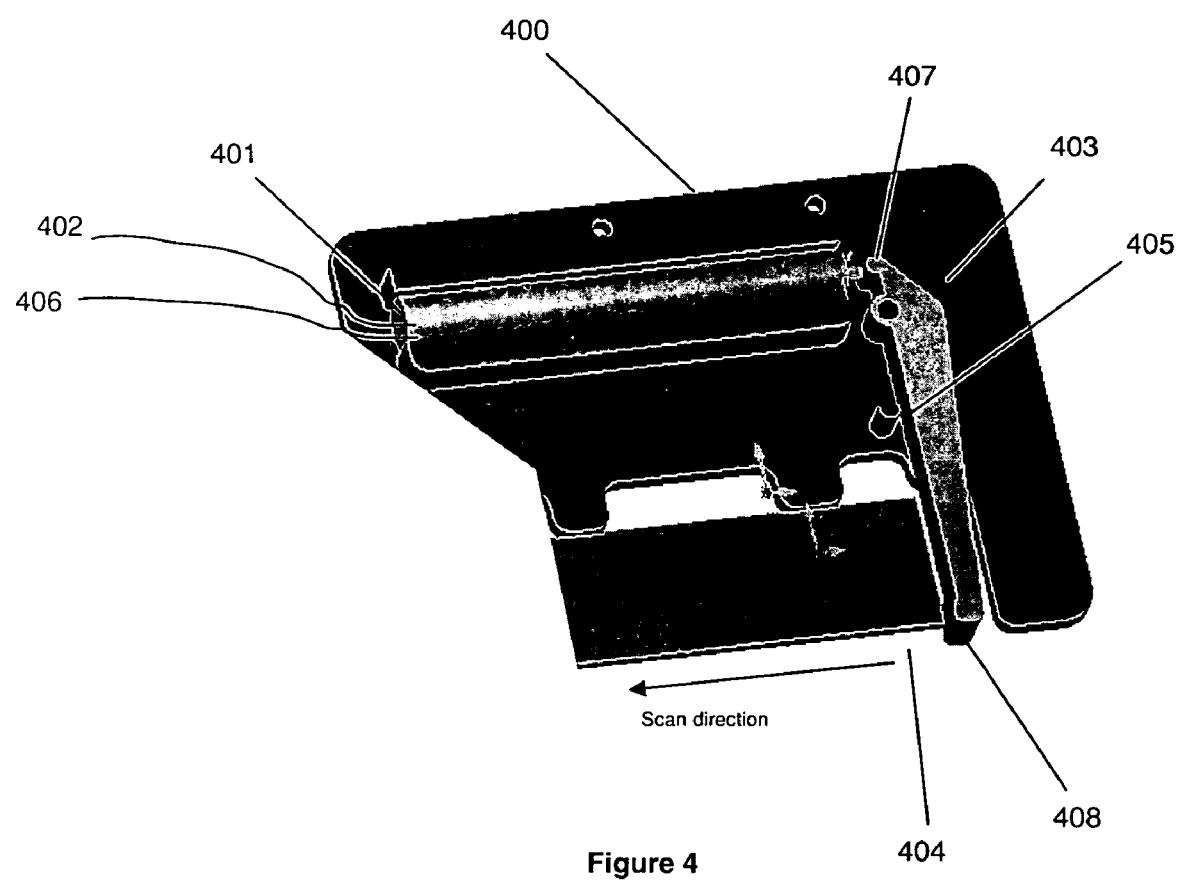
FIG. 4 illustrates an exemplary internal view of an embodiment of a piezoelectric crystal-based scanning subassembly.

As seen in FIG. 4, a representative apparatus for achieving the step of scanning the object may include a motorized stage. In this embodiment, the step of scanning the object may be achieved with a piezoelectric crystal-based stage 400 capable of moving rapidly with extremely high accuracy and high spatial resolution. One embodiment of a representative piezoelectric crystal-based apparatus is shown in FIG. 4. The apparatus in FIG. 4 incorporates a piezoelectric actuator 401 which consists of a piezoelectric crystal stack which may be controlled via a computer 402. In operation, the actuator 401 is held in contact with the cantilever 403 while the other end of the cantilever 403 is held in contact with the object holder 404. This stage subassembly is adapted to accommodate object holders 404 of different shapes. When a voltage is applied to the piezoelectric crystal stack of the actuator 401, the stack expands, applying force or otherwise pushing the cantilever at location 407. This force causes the cantilever 403 to rotate about the fulcrum 405, pushing the object holder 404 in a specified direction specified (as illustrated by the directional arrow in FIG. 4). As the voltage is reduced, the piezoelectric crystal stack of the actuator 401 contracts, pulling on the cantilever 403 at location 408. This causes rotation of the cantilever 403 about the fulcrum 405 in the opposite direction, pulling the object holder 404 back in the opposite direction.

Use of a cantilever 403 is preferred because it allows for amplification of the piezoelectric actuator motion. For example, if the piezoelectric stack of the actuator 401 expands by a distance x, then the object holder will move a distance Mx, where M is determined by the location of the fulcrum 405 of the cantilever 403 relative to the actuator 401 location. The advantage of employing a cantilever 403 in the present invention is that the object holder 404 may move significant distances without necessitating a large piezoelectric crystal stack.

For the fastest possible operation, the piezoelectric actuator 401 is run preferably in open-loop mode (i.e., no control loop to provide position feedback). In those instances where higher accuracy and repeatability are required, the piezoelectric crystal stack is equipped with a position sensor 406 to provide feedback effectively closing the loop. The closed-loop piezoelectric sensor 406 may also be controlled via a computer.

Figure 5:
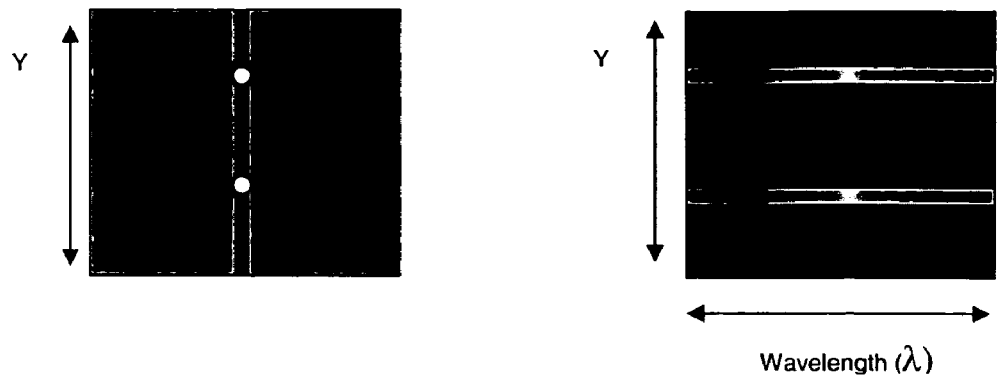
FIG. 5 illustrates an exemplary dispersed image of a single slit aperture acquired at a particular scan position.
Figure 6:
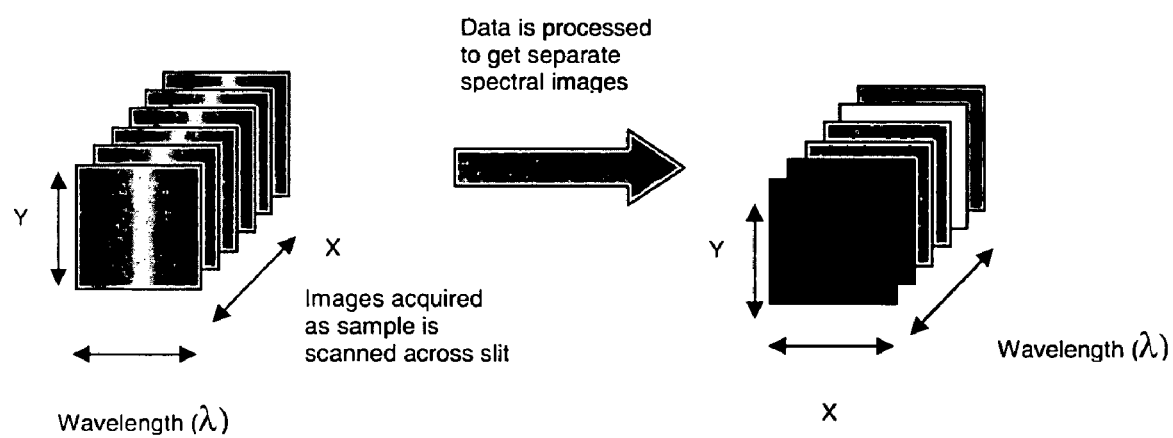
FIG. 6 illustrates an exemplary series of spectral images acquired during the scan when the present invention is operated to achieve high spectral resolution (i.e., mode #2 operation)
Figure 7A:
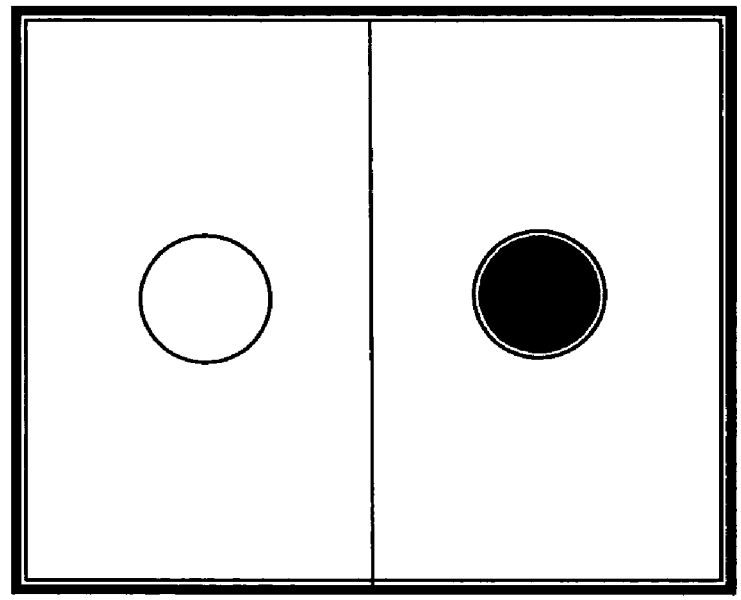
FIG. 7a illustrates, for example, two simultaneous component images acquired when the present invention is operated to achieve high temporal resolution (i.e., mode #1 operation)
Figure 7B:
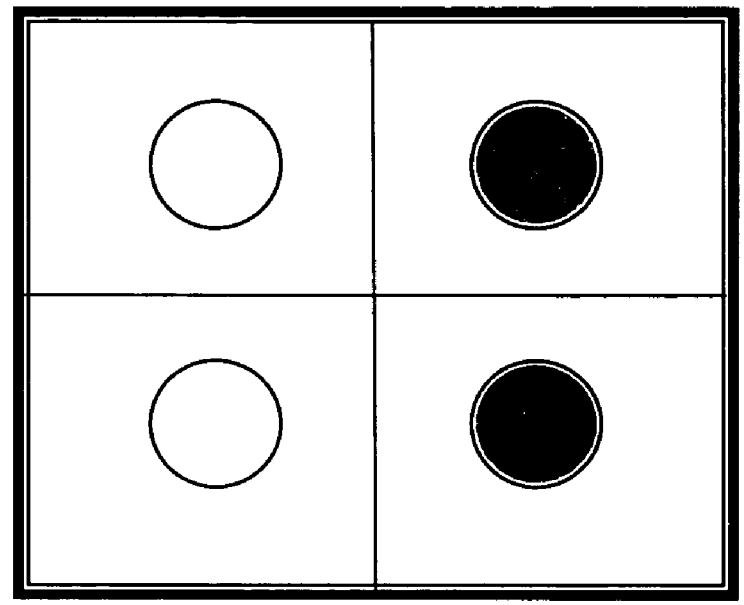
FIG. 7b illustrates, for example, four simultaneous component images acquired when the present invention is operated to achieve high temporal resolution (i.e., mode #1 operation)

The step of re-imaging the light is, in one embodiment, adapted to operate in multiple modes to achieve the separation of the light into its component optical states. In mode #2, this step may be achieved, for example, by forming a spectral image of one line (as seen in FIG. 5) or multiple lines of the object. In the single line example, as the object is scanned, spectral information for each line image is acquired as shown in FIG. 6. With the completion of the scan, a three-dimensional data cube of information is generated (x, y, and wavelength) as shown in FIG. 6, for example. In mode #1 operation, the acquisition of a data cube of information is achieved by the simultaneous acquisition of multiple images which have had their optical state modified. Examples of the acquisition of two and four simultaneous images according to mode #1 operation are shown in FIGS. 7a and 7b respectively.

Figure 8:
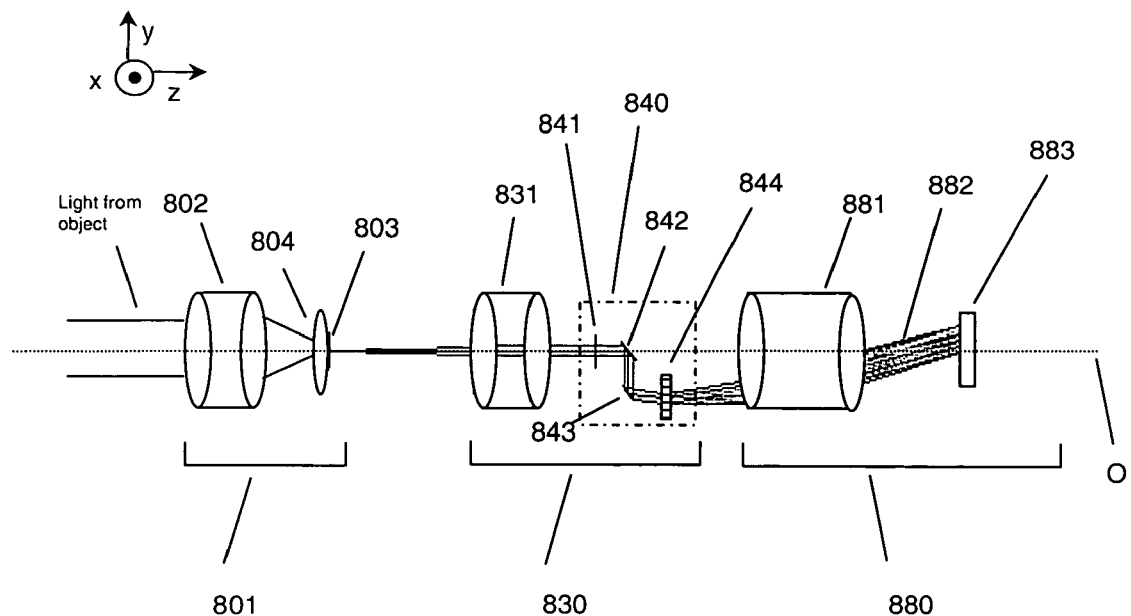
FIG. 8 illustrates an exemplary re-imaging subassembly utilizing a transmission grating based removable mechanical subassembly.

A representative apparatus for achieving the step of re-imaging the light after modifying its optical state is shown in FIG. 8. Additional descriptions of other possible embodiments for this apparatus may also be seen in U.S. Pat. Nos. 5,982,497 and 5,926,283. A representative re-imaging apparatus may comprise three subassemblies: an image collection subassembly 801, a separation subassembly 830 and an imaging subassembly 880. Preferably, in one embodiment of the present invention, the image collection subassembly 801 is adapted to produce an intermediate image of the object, the separation subassembly 830 is adapted to separate the light from each point in the image into its component optical states, while the imaging subassembly 880 is adapted to focus and record the separate component images.

As seen in FIG. 8, a representative image collection subassembly 801 may comprise a single or multi-element optic 802, an adjustable detection aperture 803, and an optional field lens 804. The single or multi-element optic 802 is preferably used to produce an image of the object at the location of the detection aperture 803. When the step of producing an image uses another optical system (e.g., a microscope), optic 802 may be part of the optical system of the microscope (e.g. a tube lens). The detection aperture 803 is preferably adjustable to micrometer level accuracies. In operation, the detection aperture 803 is preferably made very small so that only a very small portion of the image produced by the microscope is allowed to pass and as the object is scanned, a different portion of the object passes through the detection aperture. In this way, the spatial dimension of the object is acquired. An optional field lens 804 may be placed on either side of the detection aperture 803 to ensure that the exit pupil of the preceding optical system (e.g., a microscope) is positioned at the proper location within the re-imaging apparatus in order to maximize light throughput and to minimize spatial and spectral aberrations.

The separation subassembly 830 is preferably adapted to collimate the light coming from the detection aperture 803 and to separate the light into components having different optical states. In one embodiment, the separation subassembly 830 may comprise a single or multi-element optic 831 which will collimate the light from each point in the detection aperture 803. This optic 831 is preferably adapted to maximize light throughput and minimize spatial and spectral aberrations.

Following this optic is a removable mechanical subassembly 840, 940, 1040, 1140 which is adapted to achieve the different modes of operation of this apparatus and method, and may be adapted to hold or securely retain various optical components within its compact structure. For mode #2 operation of the present invention, the mechanical subassembly may include a grating 844 to separate the spectral components. When the mechanical subassembly is fully inserted into the apparatus, for example, the light passes through the grating 844 and is dispersed, allowing for the measurement of spectra. When the mechanical subassembly is moved into an intermediate position (bypass mode) or removed altogether, the grating 844 is removed from the optical path and the apparatus re-images without modifying the optical state. This "bypass mode" is extremely advantageous as it only requires that the mechanical subassembly 840, 940, 1040, 1140 be moved out of the optical path and does not require the user to remove the whole re-imaging apparatus when spectral imaging is not desired. The mechanical subassembly 840, 940, 1040, 1140 are interchangeable, thereby allowing the user to use different mechanical subassemblies for different applications.

In one example embodiment of the removable mechanical subassembly (element 840 shown in FIG. 8), the mechanical subassembly 840 may hold or securely retain various optical components. As an example, for the mode #2, the light is incident on a first reflective mirror 842 of the mechanical subassembly 840 and is reflected so that it is traveling toward a second reflective mirror 843 of the separation subassembly 830. This light is then reflected again by the second mirror 843 towards the transmission grating 844 of the mechanical subassembly 840. The second mirror 843 may be adjustable so that the angle of incidence of the reflected beam on the grating 844, and hence the diffraction angle, may be adjusted to accurately position the separated wavelength components 882 on a detector 883. The diffraction grating 844 may also be adjustable with respect to tip angle, tilt angle, rotation, and axial displacement so that dispersion vector is parallel to one dimension of the detector 883. This mechanical subassembly 840 may optionally hold one or more optical components 841 such as dichroic, amplitude, polarization beamsplitters, neutral density filters, spectral filters or polarizers to further modify the optical state of the incident light.

Figure 9:
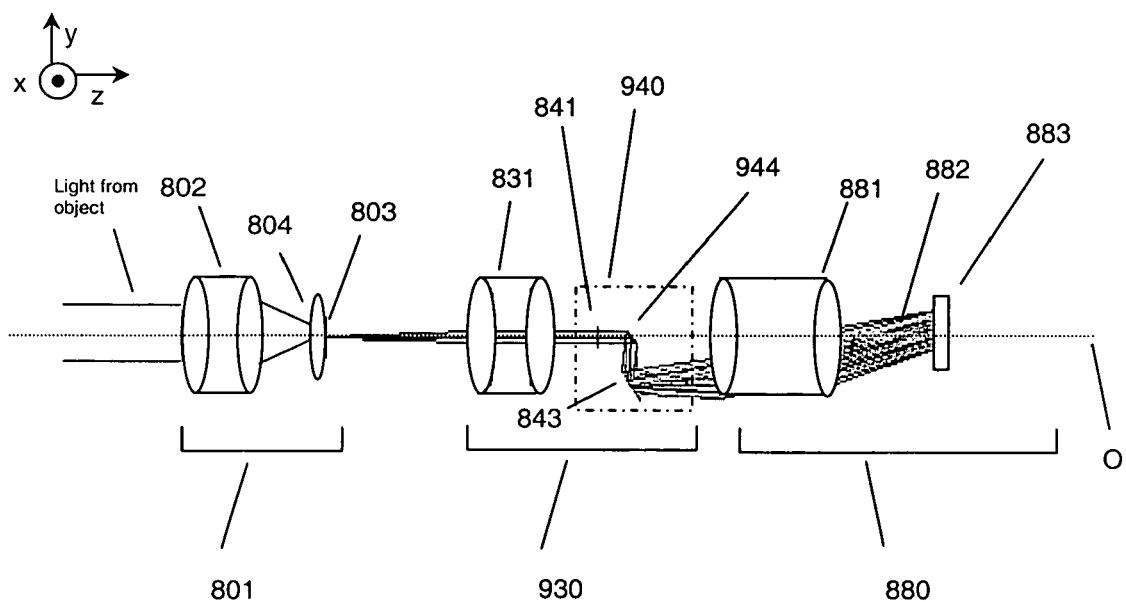
FIG. 9 illustrates an exemplary re-imaging subassembly utilizing a reflection grating based removable mechanical subassembly.

An alternative example for operation of the present invention in mode #2 is illustrated in FIG. 9. As seen in FIG. 9, the removable mechanical subassembly 940 is adapted to utilize a reflective grating 944. In this exemplary embodiment, light is incident on a reflective grating 944 and is simultaneously dispersed and reflected so that the dispersed light is traveling toward a reflective mirror 843 of the separation subassembly 930. This light is then reflected again by the mirror 843 towards the imaging subassembly 880. The tip angle, tilt angle, and axial displacement of the reflective grating 944 and reflective mirror 843 may be adjustable to achieve accurate positioning of the separated wavelength components 882 on a detector 883. The diffraction grating 944 may also be adjustable with respect to rotation so that dispersion vector is parallel to one dimension of the detector 883. This mechanical subassembly 940 may optionally hold one or more optical components 841 such as dichroic, amplitude, polarization beamsplitters, neutral density filters, spectral filters or polarizers to further modify the optical state of the incident light.

Figure 10:
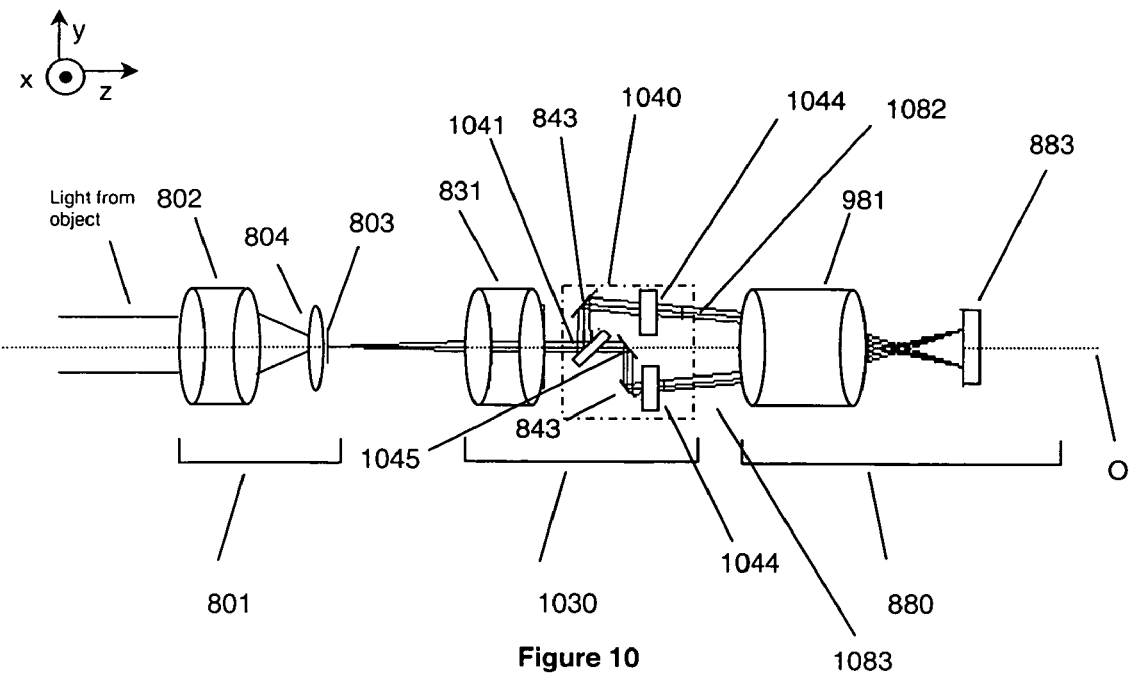
FIG. 10 illustrates an exemplary re-imaging subassembly utilizing an optical beamsplitter based removable mechanical subassembly.

In yet another example embodiment of the removable mechanical subassembly illustrated in FIG. 10, the mechanical subassembly 1040 may hold or securely retain various optical components to simultaneously produce multiple images of different optical states on a detector. As an example, for mode #1, light is incident on an optical beamsplitter 1041 or series of optical beamsplitters that separate the incident light into multiple, independent optical channels 1082 based on the properties of the beamsplitter(s). In the example illustrated in FIG. 10, a single optical beamsplitter 1041 is shown to separate the incident beam into two independent optical channels, a reflected beam and a transmitted beam 1083. The reflected beam 1082 propagates towards reflective mirror 843 of the separation subassembly 1030 and the transmitted beam propagates towards reflective mirror 1045 of the removable mechanical subassembly 1040. After reflection off of these mirrors 843,1045, the reflected beam propagates towards the imaging subassembly 980. The transmitted beam reflects off of a second reflective mirror 843 of the separation subassembly such that it is also propagating towards the imaging subassembly 980. The reflective mirrors 843 may also be adjustable with respect to tip angle, tilt angle, and axial displacement so that the multiple component images are formed on the detector 883 with accurate pixel-to-pixel registration. This mechanical subassembly 1040 may optionally hold one or more optical components 1044 such as neutral density filters, spectral filters or polarizers to further modify the optical state of the separated optical channels.

In yet another example embodiment of the removable mechanical subassembly, the mechanical subassembly may hold or securely retain various optical components to combine the imaging properties of Mode#1 and Mode#2.

Figure 11:
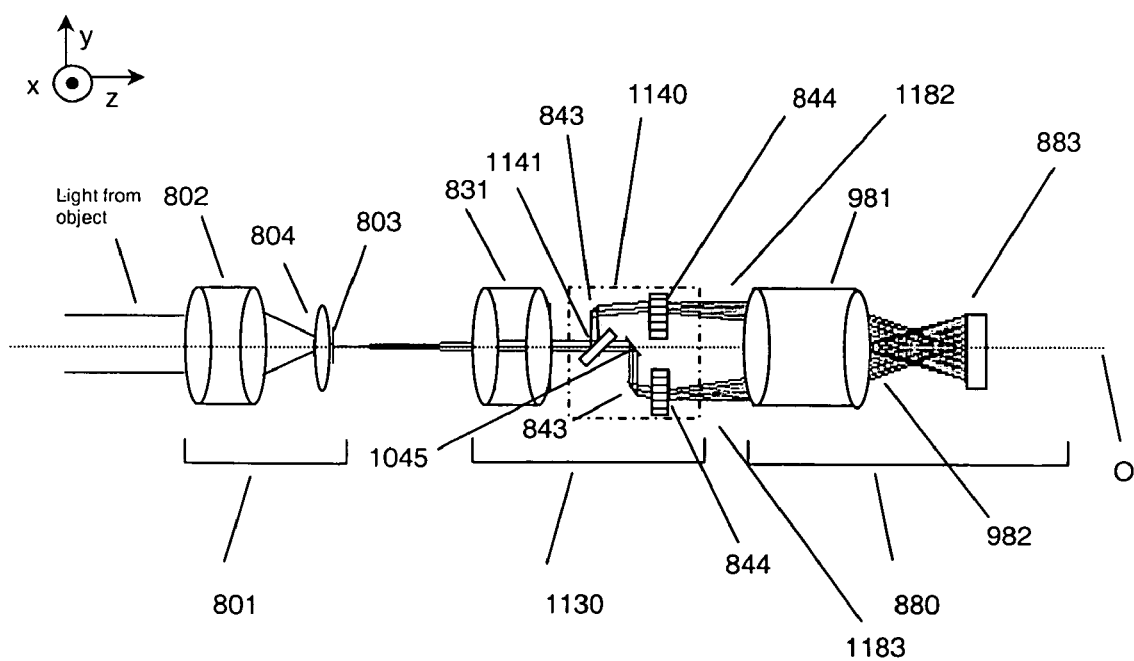
FIG. 11 illustrates an exemplary re-imaging subassembly utilizing a combination grating and beamsplitter based removable mechanical subassembly.

In one exemplary embodiment, the separation subassembly 1130 and removable mechanical subassembly 1140 of FIG. 11 would function as described in the text discussing FIG. 10. However, the optical filters 1044 of the removable mechanical subassembly 1040 would be replaced with transmission gratings 844 as shown in FIG. 11. In this way, spectra for two different optical states can be acquired simultaneously on a detector 883. As an example, if the optical beamsplitter 1141 is a polarization beamsplitter, then it will be possible to simultaneously acquire a spectral datacube for each polarization state of the incident light.

Furthermore, the polarizing beamsplitter, can be replaced with a combination of dichroics and/or polarizing beamsplitters and/or amplitude beamsplitters to yield additional wavelength and/or polarization and/or intensity channels simultaneously. Optional combinations of optical beamsplitters are disclosed, for example, in U.S. Pat. Nos. 5,982,497 and 5,926,283.

Figures 12A, 12B:
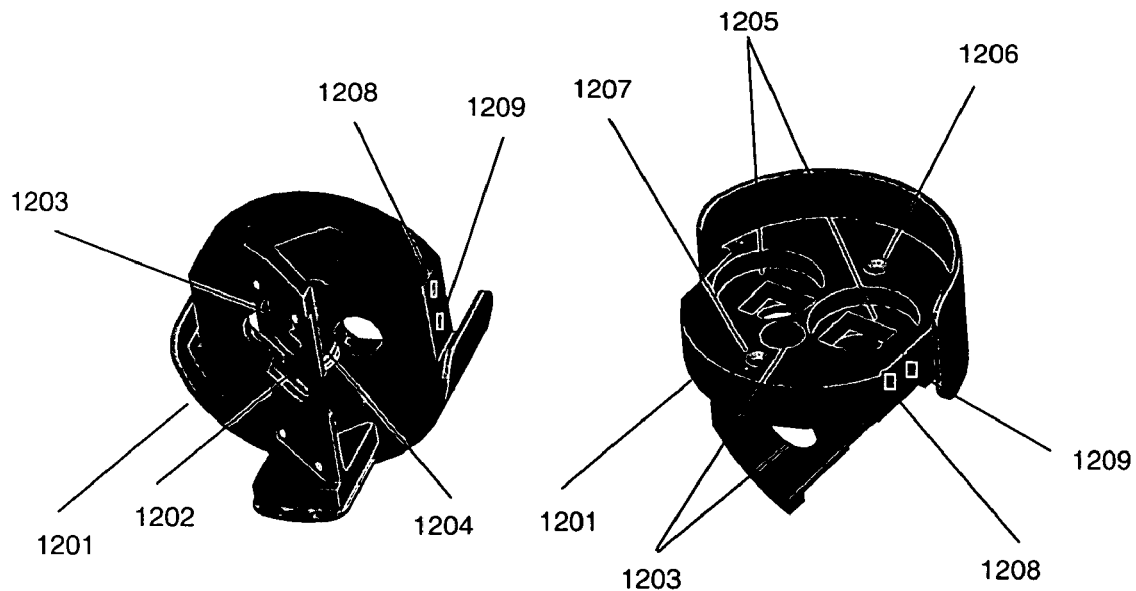
FIG. 12a illustrates an exemplary perspective of the removable mechanical subassembly.
FIG. 12b illustrates another exemplary perspective of the removable mechanical subassembly.

FIGS. 12a and 12b illustrate one embodiment of the mechanical structure for the removable mechanical subassembly 840, 940, 1040, 1140. An optical beamsplitter or series of optical beamsplitters may be held at location 1202. A reflective mirror 1045, 1145 or reflective grating 944 may be held at position 1204. When the removable mechanical subassembly is in an intermediate position for bypass mode, the light from the object passes through the holes 1203 unaffected. Transmission gratings and/or optical filters can be held at 1205. Tip angle, tilt angle, rotation, and axial displacement adjustments are located at 1206, 1207, 1208, and 1209.

After passing through the components of the removable mechanical subassembly 840, 940, 1040, 1140, the light from each point in the detection aperture 803 has been modified accordingly (e.g. separated into components of differing optical states). The function of the imaging subassembly 880 is to focus the modified optical beams onto a corresponding detector 883. For high-spectral resolution imaging, the image of the wavelengths at each point in the aperture 803 is recorded by the detector 883 and may be captured with a computer 106 so that it can be visualized and processed with the appropriate software. The imaging subassembly 880 is preferably comprised of a single or multi-element optic 881 and a detector 883 for recording the images.

Figure 13:
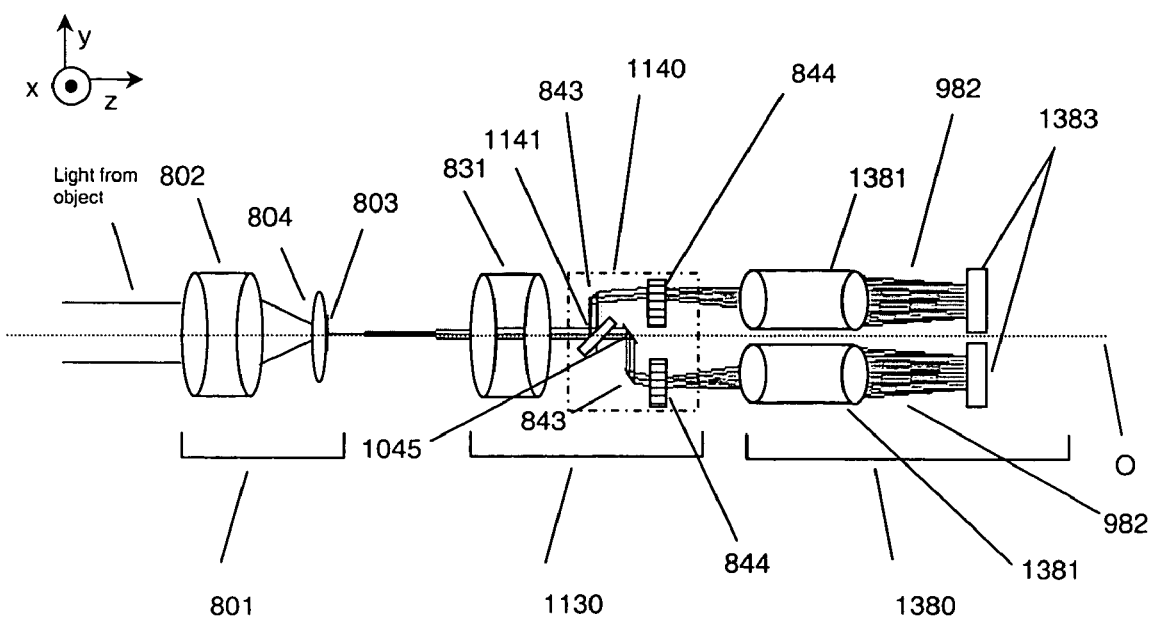
FIG. 13 illustrates an exemplary re-imaging subassembly using multiple imaging subassemblies.

In an alternative embodiment as illustrated in FIG. 13, the imaging subassembly 1380 can include separate multi-element optics 1381 and corresponding detectors 1383 so that each channel 1382 can be imaged onto a separate detector 1383. This configuration has the advantage of achieving the multiple methods of spectral imaging without sacrificing field-of-view or spectral resolution (as discussed in U.S. Pat. Nos. 5,982,497 and 5,926,283).

The present invention may be embodied as a method or an apparatus; however, those of skill in the art will now also come to realize that the present invention may also be embodied as a process or a system. Other variations and modifications of the present invention will be apparent to those of skill in the art, and is not limited except by the appended claims. The particular values and configurations discussed above can be varied, and are cited to illustrate example embodiments of the present invention. It is contemplated that the use of the present invention can involve components having different characteristics as long as the principles disclosed herein are followed. In this regard, the present system may be described herein in terms of functional block components, various processing steps or interfaces. It should be appreciated that such functional blocks may be realized by various optics, hardware, firmware, and/or software components configured to perform the specified functions. Such general functions and components that are known to those skilled in the art are not described in detail herein, but remain within the spirit, and the scope, of the present invention.

We claim:

1. A method for generating spectral images of an object in an optical system comprising the steps of:

illuminating the object with a modified illumination profile of the optical system;

producing a reflected, transmitted or fluorescence light image of the illuminated object by introducing a second optical system;

re-imaging the light image, said re-imaging step including:

receiving an intermediate image of the object along an optical axis at a position substantially coincident with an aperture, collimating the light emanating from each point in the aperture resulting in collimated light, separating the collimated light into components of differing optical states, optically filtering the separated components to further modify the optical states and remove higher dispersed orders, imaging the separate components on at least one detector; and scanning the object.

2. The method of claim 1 wherein the step of illuminating the object further comprises the step of inserting an aperture in an illumination path of the optical system at a position optically conjugate to the object to achieve one or more reduced areas of illumination on the object.

3. The method of claim 1 wherein the step of illuminating the object further comprises the step of imaging an illumination source at the location of a field stop to achieve critical illumination of the object.

4. The method of claim 1 wherein the step of illuminating the object further comprises the step of imaging an image of the illumination source at the location of a field stop to achieve critical illumination of the object.

5. The method of claim 1 where the step of separating the collimated light further includes using an interchangeable module that contains the optical components used for separation.

6. The method of claim 5 wherein the step of separating the collimated light further comprises the step of modifying the light's optical state by at least one grating.

7. The method of claim 5 wherein the step of separating the collimated light further comprises the step of modifying the light's optical state by at least one optical beamsplitter.

8. The method of claim 5 wherein the step of separating the collimated light further comprises the step of modifying the light's optical state by a combination of at least one grating and at least one optical beamsplitter.

9. The method of claim 5 wherein the interchangeable module further can be moved to an intermediate location allowing for re-imaging without modification of the light's optical state.

10. A method for generating spectral images of an object in an optical system comprising the steps of:

illuminating the object with a modified illumination profile of the optical system;

producing a reflected, transmitted or fluorescence light image of the illuminated object by introducing a second optical system;

re-imaging the light image, said re-imaging step including:

receiving an intermediate image of the object along an optical axis at a position substantially coincident with an aperture, collimating the light from each point in the aperture, dividing the light into at least two separate optical channels using at least one optical beamsplitter, dispersing the collimated light in at least once optical channel in order to separate the constituent spectra, imaging each optical channel on at least one detector, and scanning the object.

11. The method of claim 10 where the step of dispersing the light further comprises filtering the light in each channel to modify the optical state of the light or remove higher dispersed orders.

12. A method for generating spectral images of an object in an optical system comprising the steps of:

illuminating the object with a modified illumination profile of the optical system;

producing a reflected, transmitted or fluorescence light image of the illuminated object by introducing a second optical system;

re-imaging the light image on at least one detector after modifying the light's optical state to achieve both high-spectral and high-temporal resolution imaging; and scanning the object, said scanning step including:

applying a voltage to a piezoelectric crystal corresponding to expansion or contraction of the crystal, allowing the piezoelectric crystal to move an adjacent cantilever, the length of the cantilever and a position of the fulcrum about which the cantilever rotates being selected to achieve a desired resolution and amplification of the motion, and holding the object with an enclosure in mechanical communication with the cantilever.

13. The method of claim 12 where the step of scanning the object further comprises the steps of monitoring and controlling the position of the piezoelectric crystal to achieve closed-loop operation.

14. An apparatus made in accordance with the method of claim 1.

15. A method for generating spectral images of an object in an optical system comprising the steps of:

illuminating the object with a modified illumination profile of the optical system;

producing a reflected, transmitted or fluorescence light image of the illuminated object by introducing a second optical system;

re-imaging the light image on at least one detector after modifying the light's optical state to achieve both high-spectral and high-temporal resolution imaging by receiving an intermediate image of an object along an optical axis at a position substantially coincident with an aperture, collimating the light emanating from each point in the aperture resulting in collimated light, separating the collimated light into components of differing optical states, optically filtering the separated components to further modify the optical states and remove higher dispersed orders, and imaging the separate components on at least one detector; and scanning the object.

16. The method of claim 15 wherein the step of illuminating the object further comprises the step of inserting an aperture in an illumination path of the optical system at a position optically conjugate to the object to achieve one or more reduced areas of illumination on the object.

17. The method of claim 15 wherein the step of illuminating the object further comprises the step of imaging an illumination source at the location of a field stop to achieve critical illumination of the object.

18. An optical system apparatus adapted to generate spectral images of an object comprising:

at least one illuminating means adapted to illuminate the object with a modified illumination profile of the optical system;

at least one second optical system adapted to produce a reflected, transmitted or fluorescence light image of the illuminated object;

at least one light modifier adapted to modify the light image from the at least second optical system;

at least one detector adapted to re-image the light image from the light modifier to achieve both high-spectral and high-temporal resolution imaging, the wherein the at least one detector is adapted to re-image the light image by receiving an intermediate image of an object along an optical axis at a position substantially coincident with an aperture, collimating the light emanating from each point in the aperture resulting in collimated light, separating the collimated light into components of differing optical states, optical filtering the separated components to further modify the optical states and remove higher dispersed orders, and imaging the separate components on the at least one detector; and scanning means adapted to scan the object.

* * * * *